United States Patent [19]
Reese

[11] Patent Number: 5,409,486
[45] Date of Patent: Apr. 25, 1995

[54] DOUBLE THREADED ARTHRODESIS SCREW

[75] Inventor: H. William Reese, Tempe, Ariz.

[73] Assignee: Phoenix Surgical Products, Inc., Peoria, Ariz.

[21] Appl. No.: 47,197

[22] Filed: Apr. 16, 1993

[51] Int. Cl.⁶ .............................................. A61B 17/56
[52] U.S. Cl. ..................... 606/73; 411/389; 411/187; 411/397
[58] Field of Search ............ 606/72, 73, 74, 104, 606/105, 65, 66, 59; 411/389, 187, 956, 957, 399, 397

[56] References Cited

U.S. PATENT DOCUMENTS

| | | | |
|---|---|---|---|
| 4,059,102 | 11/1977 | Devas | 606/73 |
| 4,723,541 | 2/1988 | Reese | 606/73 |
| 4,796,612 | 1/1989 | Reese | 606/72 |
| 4,903,692 | 2/1990 | Reese | 606/99 |

FOREIGN PATENT DOCUMENTS

| | | | |
|---|---|---|---|
| 355035 | 2/1990 | European Pat. Off. | 606/59 |
| 502698 | 9/1992 | European Pat. Off. | 606/73 |
| 2674119 | 9/1992 | France | 606/65 |
| 89/09030 | 10/1989 | WIPO | 606/73 |

Primary Examiner—Tamara L. Graysay
Attorney, Agent, or Firm—Antonio R. Durando; Harry M. Weiss

[57] ABSTRACT

A straight, double-threaded arthrodesis screw that comprises a threaded compression nut mounted thereon. The screw consists of a shank containing distal right-handed threads for screwable connection with a threaded hole in the bone, proximal left-handed threads on which the compression nut is screwably mounted, and a longitudinal perforation for engagement with an installation tool. A hole is first drilled and tapped in the bone to provide an internal right-handed thread conforming to the distal threads of the arthrodesis screw. The screw is installed on the bone by screwably mounting its distal portion in the hole. The compression nut is then rotated toward the proximal cortex of the bone until it contacts the soft tissue surrounding the hole in the bone. The soft tissue is secured in place between the compression nut and the bone's cortical surface by further screwing the distal threads into the bone while preventing the compression nut from turning with respect to the clamped tissue. The proximal excess portion of the screw is then cut and removed along with the installation tool. In another embodiment of the invention for use as a clamping device for fractured bone parts, the arthrodesis screw is passed through a perforation across the bone fracture and the distal threads of the screw are mounted on a distal portion of the fractured bone; a modified compression nut is then forced into the perforation in the proximal portion of the fractured bone and tightened to provide a retaining arthrodesis clamp.

14 Claims, 1 Drawing Sheet

DOUBLE THREADED ARTHRODESIS SCREW

BACKGROUND OF THE INVENTION

1. Field of the Invention

This invention is related in general to the field of orthopedic devices and methods for joining parts of fractured bones and/or soft tissue to bone cortex. In particular, the invention provides a method of performing these tasks by using a novel double-threaded screw and compression nut assembly.

2. Description of the Related Art

When bones are either fractured by accident or severed by surgical procedure, the healing process requires that they be rejoined and kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body is then minimized by a cast, brace or splint in order to promote healing and avoid mechanical stresses that may cause the bone parts to come apart during normal or necessary bodily activity. The surgical procedure of attaching two or more parts of a bone with a pin-like device or screw requires an incision in the tissue surrounding the bone and the drilling of a hole through the bone parts to be joined, often with little space to operate without inflicting further injury to the patient. Therefore, it is very important that the arthrodesis device used be capable of quick installation with a simple procedure. U.S. Pat. Nos. 4,796,612 (1988) and No. 4,903,692 (1990) to Reese describe a bone clamp and a corresponding installation tool that enable a surgeon to easily drive a pin through an aperture in two or more parts of a bone and lock it in place by means of a self-locking button placed around the shaft of the pin. The tip of the pin has a hook that engages the distal cortical surface of the bone after protruding through the aperture in the bone. This bone clamp and installation tool provide an efficient method for clamping fractured bones together, but they have been found to be unsatisfactory when relatively great pressure is required to push the self-locking button toward the proximal bone cortex. In addition, the ability to make fine adjustments of the clamping force is limited by the step-like operation of the ratchet-type self-locking mechanism provided.

Accordingly, an improved device based on the same concept was developed and is described in my application Ser. No. 977,074, currently pending. This invention includes continuous threads over which the button may be either pushed forward or screwed, thus allowing for finer clamping pressure adjustments. A remaining problem arises from the fact that, in order to achieve these fine pressure adjustments, the button has to be rotated with respect to the proximal cortex over which it applies pressure. Thus, some unwanted scraping and damage to the adjacent tissue occurs.

The present invention is directed at solving the same problems by means of a different mechanism that is suitable for providing arthrodesis between either fractured parts of a bone or the cortex of a bone and the surrounding soft tissue. This invention consists of a screw-type arthrodesis device and installation tool that achieve the same functional characteristics of the prior-art devices without some of the drawbacks and with a much simpler design and relatively inexpensive costs of manufacture.

SUMMARY OF THE INVENTION

One objective of this invention is the development of an arthrodesis device and method of application that simplify the process of installation in a fractured bone.

Another goal of the invention is a double-threaded arthrodesis device that can be inserted through an aperture in one or more bones and locked firmly in place by the tightening action of the two threads without scraping of the surrounding tissue.

Yet another goal of the invention is a simple arthrodesis device that consists of only two components, a double-threaded screw and a compression nut, wherein the clamping action of the compression nut is concurrent with the positioning action of the screw.

Still another objective is an arthrodesis device that can be securely tightened and that can provide a clamping action between fractured bone segments without passing the device entirely through the bone parts that are being joined.

Another objective of the invention is an arthrodesis device that can be used not only to connect two or more bone parts, but also to clamp soft tissue to the cortical surface of the bone.

A final objective is the easy and economical manufacture of the device according to the above stated criteria. This is achieved by using commercially available components and materials, modified only to the extent necessary to fit the requirements of the invention.

Therefore, according to these and other objectives, the present invention consists of a straight, double-threaded arthrodesis screw having a threaded compression nut mounted thereon. The screw consists of a shank containing distal right-handed threads for screwable connection with a threaded hole in the bone, proximal left-handed threads on which the compression nut is screwably mounted, and a longitudinal perforation for engagement with an installation tool. A hole is first drilled and tapped in the bone to provide an internal right-handed thread conforming to the distal threads of the arthrodesis screw. The screw is installed on the bone by screwably mounting its distal portion in the hole. The compression nut is then rotated toward the proximal cortex of the bone until it contacts the soft tissue surrounding the hole in the bone. The soft tissue is secured in place between the compression nut and the bone's cortical surface by further screwing the distal threads into the bone while preventing the compression nut from turning with respect to the clamped tissue. The proximal excess portion of the screw is then cut and removed along with the installation tool. In another embodiment of the invention for use as a clamping device for fractured bone parts, the arthrodesis screw is passed through a perforation across the bone fracture and the distal threads of the screw are mounted on a distal portion of the fractured bone; a modified compression nut is then forced into the perforation in the proximal portion of the fractured bone and tightened to provide a retaining arthrodesis clamp.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

DESCRIPTION OF THE PREFERRED EMBODIMENTS

The most important inventive feature of this disclosure is the recognition that a double-threaded screw-like shank can be used to provide clamping between the distal portion of the shank and a compression nut screwed on its proximal portion without rotation of the nut with respect to the bone or tissue to which it is engaged. This feature permits fine adjustments to the clamping tension of the nut without causing unnecessary scraping of the clamped surface. In addition, it permits the use of the compression nut as a tissue clamping device.

Figure 1:
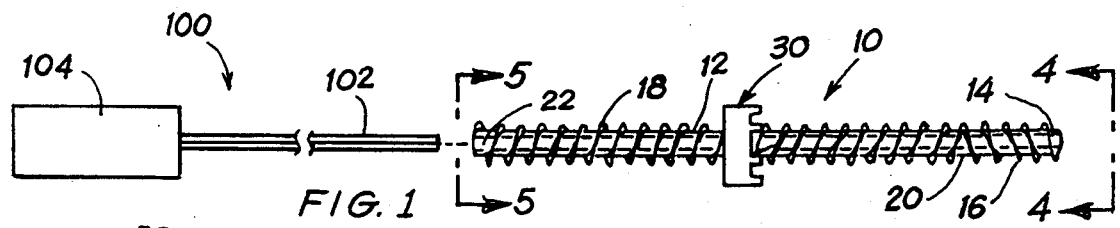
FIG. 1 is a side elevational view of an arthrodesis-screw/compression-nut assembly and of a partially cut-out installation tool therefor according to the preferred embodiment of the invention.
Figures 2, 3, 4, 5:
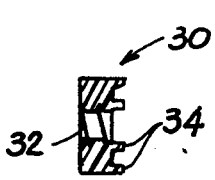
FIG. 2 is a schematic view of a bone portion containing a threaded hole for engagement with the threaded distal portion of the arthrodesis screw of FIG. 1.
FIG. 3 is a cross-sectional view of the compression nut shown in FIG. 1.
FIG. 4 is an end view of the arthrodesis screw of the invention taken from line 4—4 in FIG. 1.
FIG. 5 is an end view of the arthrodesis screw of the invention taken from line 5—5 in FIG. 1.

Referring to the drawings, wherein like parts are designated throughout with like numerals and symbols, FIG. 1 illustrates in elevation a side view of an arthrodesis-screw/compression-nut device 10 and of an installation tool 100 therefor (partially cut-out along the length of its shaft) according to the preferred embodiment of the invention. The device 10 is designed for clamping soft tissue to a bone and comprises a screw 12 and a compression nut 30 screwably mounted thereon. The screw 12 consists of a straight shank 14 having two sets of threads along its length. The distal portion of the shank contains a right-handed set of distal threads 16 for screwable connection with conforming receiving threads in a perforated bone. FIG. 2 illustrates in cross-section the cortex of a bone 50 and surrounding tissue 52 wherein a perforation 54 has been drilled and right-handed threads 56 have been tapped. The number of distal threads 16 in the screw 12 is limited to the minimum required to ensure the desired degree of coupling with the bone, as these threads are intended to be fully contained within the bone during application, as explained in detail below. The proximal portion of the shank contains a left-handed set of proximal threads 18 for screwable connection with the compression nut 30. This nut contains axial left-handed threads 32 that conform to the proximal threads 18 of the screw, as shown in the cross-sectional view of FIG. 3. Thus, the nut 30 can be mounted on the proximal portion of the screw 12 and rotated counterclockwise to move longitudinally toward the distal portion of the screw all the way to the point 20 along the shank 14 where the left-handed threads end.

The screw 12 is rather small, typically having a shank diameter of approximately 2 millimeters and a distal thread diameter of about 4 millimeters. Although not critical to the invention, the proximal threads 18 of the screw are typically of the same diameter as the distal threads 16. Any material capable of withstanding the stresses generated by clamped portions of bone is suitable for construction, but typical materials consist of synthetic polymers that tend to be flexible and cannot withstand much axial twisting without deformation. Therefore, the preferred embodiment of the screw of the invention comprises a longitudinal guide-hole 22 throughout the length of the shank, which is adapted to receive and interlock with the conforming shaft 102 of the installation tool 100. As seen in the end views of FIGS. 4 and 5, the cross-section 24 of the guide-hole (and therefore of the corresponding shaft) is shown as square for purposes of illustration, but any Allen-type connection (hex connection), or other equivalent connection, would be suitable to provide the coupling required to drive the screw into the bone. The shaft 102 of the installation tool is inserted all the way to the distal end of the guide-hole 22, so that maximum longitudinal rigidity and optimal distribution of the torque applied to the screw is obtained.

Thus, the soft-tissue arthrodesis device of this invention is applied by first drilling a hole in the bone 50 where soft tissue 52 needs to be attached, as illustrated in FIG. 2. The perforation 54 needs to be longer than the distal portion of the screw 12, so that the distal threads 16 may be entirely anchored in the bone. A perforation approximately 2 mm in diameter and about 20 to 25 mm long is typical for soft-tissue arthrodesis. Conforming threads 56 (typically 4 mm in diameter) are then tapped into the perforation for screwable engagement with the distal threads 16 of the screw. Once the bone site has been so prepared, the shaft 102 of the installation tool 100 is inserted through the guide-hole 22 of the screw (all the way to its distal end) and used to insert and completely screw the distal portion of the screw 12 into the bone by clockwise rotation of the tool's handle 104. As soon as the threads 16 are completely embedded in the bone, the clockwise rotation should stop to avoid insertion of any proximal threads 18 into the bone perforation. In fact, in order to ensure that this does not happen, it is recommended that the screw be turned counterclockwise (unscrewed) by a small amount (such as one or two turns, depending on the threads pitch) after the distal threads have been completely inserted into the bone. In addition, the proximal threads 18 may be provided with a diameter no greater than the diameter of the perforation 54, so that they may be advanced into the bone without causing damage to the threads 56 in the bone perforation.

Figures 6, 8:
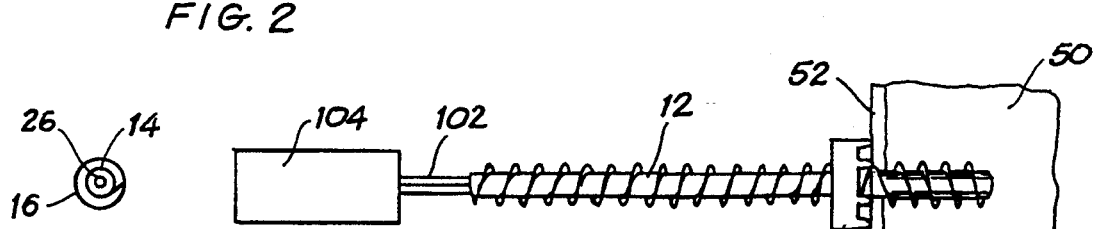
FIG. 6 is an elevational view illustrating the screw and compression nut of FIG. 1 after installation in the bone perforation shown in FIG. 3. For clarity, the portion of the screw embedded in the bone is shown as it would be seen in X-ray images.
FIG. 8 is an end view of the arthrodesis screw of the invention taken from line 4—4 in FIG. 1 and showing a restriction of the guide-hole of the invention to form a distal-end pinhole aperture.

The compression nut 30 is now turned counterclockwise around the screw to advance the nut toward the bone along the proximal threads 18. As the nut approaches the bone, the soft tissue 52 surrounding the bone perforation 54 is collected and stretched toward the screw so that it is within the reach of a plurality of retaining spikes 34 distributed peripherally in the side of the nut facing the bone. The nut is then rotated delicately until enough pressure is exerted by the spikes on the soft tissue to keep the tissue in place without causing damage to it. At this point, the nut 30 is held firmly in place in rotational relation to the tissue and the screw 12 is further rotated clockwise, gently and only to the extent necessary to secure the clamping of the soft tissue to the bone. Because of the double action of the two sets of threads in the screw, a small amount of rotation of the screw is sufficient to cause the nut 30 to firmly lock the tissue in place without any damage to the tissue. The resulting configuration is illustrated in FIG. 6, where the distal portion of the screw 12 is shown for clarity as it would be seen in X-ray images. Finally, the shaft 102 of the tool is extracted from the guide-hole 22 and the screw is cut flush with the external side of the compression nut 30, as illustrated in FIG. 7.

In a different embodiment of the invention, the cross-section of the guide-hole 22 is restricted to form a pinhole aperture 26 at the distal end of the screw in order to prevent the shaft 102 of the installation tool from protruding forward into the bone. This geometry is illustrated in the end view of FIG. 8. Inasmuch as often surgeons prefer an installation tool having a key-wire protruding forward past the distal end of the screw 12 during installation in order to better guide the tool through the opening in the bone, such a feature may be provided with the modified tool shaft shown in the enlarged cut-out view of FIG. 9. A straight coaxial key-wire 106 is added to the end of the shaft and is sized for passage through the pinhole aperture 26 when the tool is pushed through the guide-hole 22, so that the wire protrudes forward as the shaft 102 abuts against the restriction in the distal end of the screw.

The same general concept of a double-threaded arthrodesis device is used to clamp severed parts of a bone. The screw 12 is anchored in one portion of the bone while a modified compression nut is tightened against the other, thus forming a clamp between the two portions. As illustrated in the cross-sectional view of FIG. 10, the modified compression nut 70 consists of a forward tapered conical structure threaded for screwable engagement with the proximal threads of the screw 12. The nut 70 is so designed to provide a compressive fit in a hole drilled in a fractured bone.

Figures 7, 9, 10, 11:
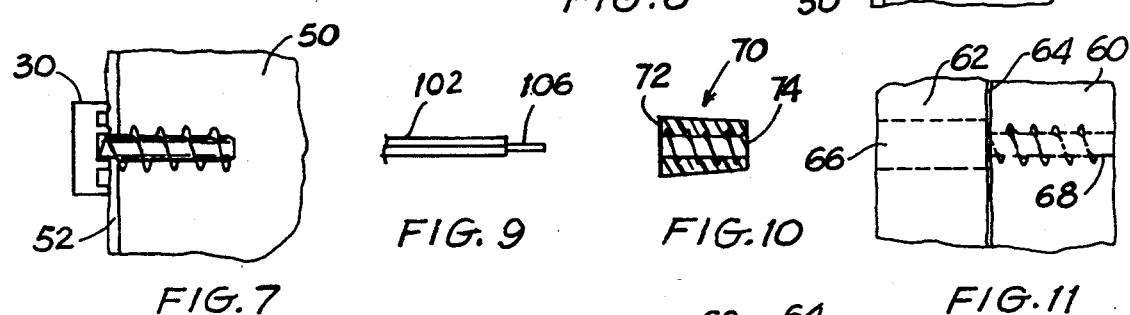
FIG. 7 is the same view of FIG. 6 where the arthrodesis screw has been cut after tightening of the compression nut against the soft tissue surrounding the bone cortex.
FIG. 9 is a partial and enlarged view of a modified shaft in the installation tool comprising a coaxial key-wire extending forward from the distal end thereof.
FIG. 10 a cross-sectional view of a modified compression nut according to another embodiment of the invention for use in clamping portions of a fractured bone.
FIG. 11 is a schematic view of two portions of a fractured bone containing a perforation therethrough and a threaded hole for engagement with the threaded distal portion of the arthrodesis screw of the invention.

Referring to FIG. 11, the distal portion 60 and the proximal portion 62 of a bone that has been severed by a fracture along the line 64 are illustrated. A proximal perforation 66 is first drilled in the proximal portion 62 in a size smaller than the larger end 72 of the conical nut 70, but sufficiently large to permit the introduction of the screw 12 through the hole. Typically, the diameter of the perforation 66 is approximately equal to that of the distal and proximal threads in the screw. A smaller perforation 68 is then drilled in the distal portion 60 of the bone in a size corresponding to the diameter of the shank 14 of the screw. The perforation 68 is then tapped to produce threads conforming to the distal threads 16 in the screw (shown schematically in the figure).

Figure 12:
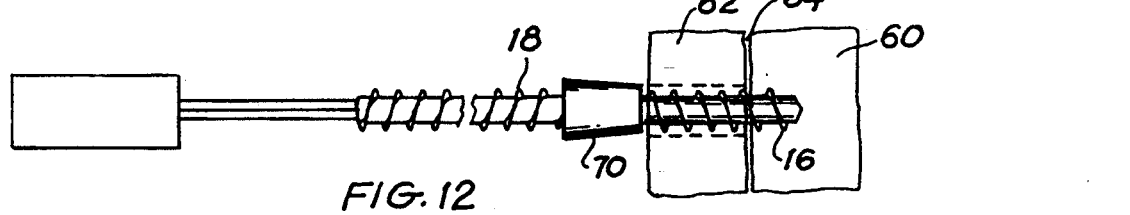
FIG. 12 is a schematic elevational view illustrating the screw of the invention with the modified compression nut of FIG. 10 partially installed in the bone illustrated in FIG. 11. For clarity, the portion of the screw embedded in the bone is shown as it would be seen in X-ray images.
Figures 13, 14:
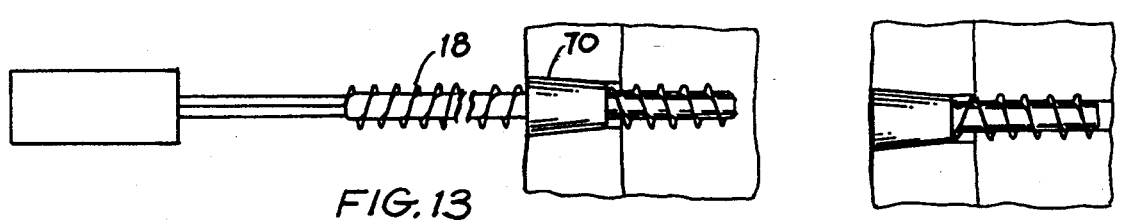
FIG. 13 illustrates the configuration of the assembly of FIG. 12 after the compression nut has been tightened against the proximal portion of the fractured bone and embedded therein.
FIG. 14 is the same view of FIG. 13 where the arthrodesis screw has been cut.

Using the installation tool as described above, the length of the distal threads 16 of the screw 12 is screwed into the distal portion 60 of the bone, thus anchoring the screw to the bone, as illustrated schematically in FIGS. 12-14. The conical compression nut 70 is then rotated counterclockwise to advance it toward the proximal portion 62 of the bone until it comes into contact with it. At this point, the nut 70 is held in stationary rotational relationship with respect to the surrounding bone and tissue and the screw 12 is rotated clockwise to cause the embedding of the nut into the bone and a clamping action between the anchored distal threads 16 (which are attached to one portion of the bone) and the compression nut (which is attached to the other portion of the bone). In order to facilitate the final step of embedding the nut, it is preferable to first rotate the screw counterclockwise a few turns before positioning the nut against the bone, and then screw the nut clockwise while holding the nut still for the final clamping step. Again, because of the double action of the two sets of threads in the screw, a small amount of rotation is sufficient to firmly implant the nut 70 into the perforation 66 in the proximal portion of bone to ensure a strong clamping action. The shaft 102 of the tool is then extracted from the guide-hole 22 and the screw is cut flush with the external side of the compression nut 70, as illustrated in FIG. 14.

In order to avoid the final step of cutting the screw flush with the external side of the compression nut 70, the length of the proximal portion of the shank 14 may be limited to the thickness of the proximal portion 62 of the fractured bone. This will ensure that the proximal end of the screw remains within the compression nut after final tensioning. In order to add flexibility to the use of such a fixed-length screw, a longer compression 70 may also be provide (2 to 3 times its average diameter), so that thicker proximal bone fragments may be clamped. In addition, as in the case of the first embodiment, the proximal threads 18 may be provided with a diameter equal to or smaller than the diameter of the perforation 68 in the distal portion 60 of the bone, so that the proximal threads may be advanced without interference with the threads in the bone.

As would be obvious to those skilled in the art, the described use of this embodiment of the arthrodesis screw of the invention requires that the smaller end 74 of the conical cross-section of the nut 70 be smaller than the diameter of the threads 16 and 18, while the larger end 72 must be larger than the diameter of the perforation 66 drilled in the proximal portion 62 of the bone. In typical use, the perforation 66 will be approximately 4 mm in diameter and the perforation 68 will be 2 mm in diameter with 4 mm threads; the nut 70 will have a tapered profile with a larger end 72 about 5 mm and a smaller end 74 about 4 mm in diameter, respectively. The nut will be about 4 to 15 mm long. The typical lengths of the distal and the proximal portions of the screw are 4–6 mm and 15–30 mm, respectively, for either embodiment of the invention. All of these dimensions, of course, would vary with the requirements of specific anatomical applications.

Thus, in use this invention permits the clamping of parts of bone or soft tissue and bone with minimally invasive surgery. The invention has been described in all embodiments as having right-handed threads in the distal portion of the screw and correspondingly in the perforations drilled into the bone, and having left-handed threads in the proximal portion of the screw and in the corresponding compression nut. It is obvious, though, that the reverse could be used equivalently to practice the invention. The important feature is the presence of double threads that permit the tightening of the compression nut without requiring its rotation with respect to the surrounding bone and tissue.

All embodiments described herein may be implemented with any of the materials currently in use for implant construction, both of the absorbable and non-absorbable type. The screw and compression nut assembly can be manufactured with standard permanent implant material, such as silicone, polypropelyne, nylon, or metals. Alternatively, they may be manufactured with absorbable materials such as those in the family of resorbable polyesters. For example, materials like polylactic acid (also known as polylactide or PLA), polyglycol acid (polyglycolide or PGA), trimethyl carbonate, and mixtures thereof are resorbable polymers currently marketed by the Birmingham Polymer Company of Birmingham, Ala. These polymers have mechanical properties equivalent to those of conventional implant materials, but over time are assimilated by the body and become entirely absorbed into the tissue surrounding the implant. It is anticipated that this gradual absorption of the implant may stimulate an ingrowth of fibrous tissue to replace implant polymer as it disappears, so as to produce a natural reconstruction of the bone and surrounding soft tissue to sustain a strong bond between the clamped parts.

While the embodiments shown in the figures feature the specific shapes therein described, the invention can obviously take other shapes with equivalent functionality and utility. In fact, any shape for any of the components that retains the functional characteristics described above provides an acceptable apparatus to practice the invention. Thus, various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and methods.

I claim:

1. A double-threaded arthrodesis screw assembly for providing a clamping connection to a bone containing a threaded perforation of a first predetermined diameter, comprising:
    (a) an elongated screw consisting of a shank with a diameter approximately equal to the diameter of the perforation in the bone, said shank having a distal portion containing distal threads for screwable connection with the threaded perforation of the bone and having a proximal portion containing proximal threads of a second predetermined diameter, said distal and proximal threads having opposite directions; and
    (b) a compression nut containing axial threads that conform to said proximal threads for screwable engagement therewith;
    wherein said compression nut consists of a longitudinal section of a cone having a smaller distal cross-section with a diameter approximately equal to the diameter of said proximal threads and having a larger proximal cross-section with a diameter larger than the diameter of said proximal threads.

2. The arthrodesis screw assembly recited in claim 1, further comprising a longitudinal guide-hole within said elongated screw, said guide-hole having a guide-hole cross-section conforming to a cross-section of an installation tool used during application of the screw.

3. The arthrodesis screw assembly recited in claim 2, further comprising an installation tool consisting of a handle and a shaft attached thereto, said shaft having a shaft cross-section conforming to said guide-hole cross-section for interlocking engagement therewith.

4. The arthrodesis screw assembly recited in claim 1, wherein said shank has a diameter of approximately 2 mm and said distal and proximal threads have a diameter of about 4 mm.

5. The arthrodesis screw assembly recited in claim 1, wherein said shank has a diameter of approximately 2 mm, said distal threads have a diameter of about 4 mm, and said proximal threads have a diameter of about 2 mm.

6. The arthrodesis screw assembly recited in claim 5, wherein said compression nut is about 10 mm long, said distal cross-section diameter is approximately 4 mm and said proximal cross-section diameter is about 5 mm.

7. A method of providing a clamping connection of soft tissue to a bone by means of a double-threaded arthrodesis screw assembly, comprising the following steps:
    (a) providing an elongated screw consisting of a shank with a first predetermined diameter, said shank having a distal portion containing distal threads of a second predetermined diameter and a proximal portion containing proximal threads of a third predetermined diameter, wherein said distal and proximal threads have opposite directions;
    (b) providing a compression nut containing axial threads that conform to said proximal threads for screwable engagement therewith;
    (c) drilling a perforation into the bone of a diameter approximately equal to said first predetermined diameter of the shank;
    (d) tapping said bone perforation to form threads conforming to said distal threads;
    (e) screwing said distal threads into said threaded perforation in the bone;
    (f) rotating said compression nut until the nut contacts the soft tissue;
    (g) holding the nut in stationary position in rotational relation to the tissue and rotating the screw to further advance the screw into the bone, thus providing clamping of the soft tissue to the bone; and (h) if necessary, cutting any part of the proximal portion of the screw that protrudes outside of the compression nut.

8. The method of claim 7, further comprising the step of providing a longitudinal guide-hole within said elongated screw, said guide-hole having a guide-hole cross-section conforming to a cross-section of an installation tool; inserting the installation tool in said guide-hole to hold and rotate the screw during steps (e) and (g); and extracting the installation tool prior to step (h).

9. The method of claim 8, further comprising the step of providing an installation tool consisting of a handle and a shaft attached thereto, said shaft having a shaft cross-section conforming to said guide-hole cross-section for interlocking engagement therewith; using the installation tool to hold and rotate the screw during steps (e) and (g); and extracting the installation tool prior to step (h).

10. The method of claim 7, wherein said compression nut is provided with a plurality of retaining spikes distributed peripherally on a side of the nut facing the bone, and wherein said spikes are used to firmly clamp the tissue to the bone during step (g).

11. A method of providing a clamping connection between a distal portion and a proximal portion of a fractured bone by means of a double-threaded arthrodesis screw assembly, comprising the following steps:

(a) providing an elongated screw consisting of a shank with a first predetermined diameter, said shank having a distal portion containing distal threads of a second predetermined diameter and a proximal portion containing proximal threads of a third predetermined diameter, wherein said distal and proximal threads have opposite directions;

(b) providing a compression nut containing axial threads that conform to said proximal threads for screwable engagement therewith;

(c) drilling a proximal perforation into the proximal portion of the bone, said proximal perforation having a diameter approximately equal to said third predetermined diameter of the proximal threads;

(d) drilling a distal perforation into the distal portion of the bone, said distal perforation having a diameter approximately equal to said first predetermined diameter of the shank;

(e) tapping said distal perforation to form threads conforming to said distal threads of the shank;

(f) screwing said distal threads into said threaded perforation in the distal portion of the bone;

(g) rotating said compression nut until the nut contacts the proximal portion of the bone;

(h) holding the nut in stationary position in rotational relation to the proximal portion of the bone and rotating the screw to further advance the screw into the bone, thus providing clamping between the proximal and distal portions of the bone; and (i) if necessary, cutting any part of the proximal portion of the screw that protrudes outside of the compression nut.

12. The method of claim 11, further comprising the step of providing a longitudinal guide-hole within said elongated screw, said guide-hole having a guide-hole cross-section conforming to a cross-section of an installation tool; inserting the installation tool in said guide-hole to hold and rotate the screw during steps (f) and (h); and extracting the installation tool prior to step (i).

13. The method of claim 12, further comprising the step of providing an installation tool consisting of a handle and a shaft attached thereto, said shaft having a shaft cross-section conforming to said guide-hole cross-section for interlocking engagement therewith; and using the installation tool to hold and rotate the screw during steps (f) and (h); and extracting the installation tool prior to step (i).

14. The method of claim 11, wherein said compression nut is provided with a smaller distal cross-section having a diameter approximately equal to the diameter of said proximal threads and a larger proximal cross-section with a diameter larger than the diameter of said proximal threads.

* * * * *